United States Patent
Tzikas et al.

(10) Patent No.: US 6,953,846 B2
(45) Date of Patent: Oct. 11, 2005

(54) PYRIDONE DYES, A PROCESS FOR THEIR PREPARATION AND THEIR USE IN THE PRODUCTION OF COLORED PLASTICS OR POLYMERIC COLOR PARTICLES

(75) Inventors: Athanassios Tzikas, Pratteln (CH); Urs Lauk, Zürich (CH); Romeo Dreier, Fehren (CH); Antoine Clément, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 35 days.

(21) Appl. No.: 10/469,889

(22) PCT Filed: Feb. 28, 2002

(86) PCT No.: PCT/EP02/02150

§ 371 (c)(1),
(2), (4) Date: Sep. 5, 2003

(87) PCT Pub. No.: WO02/072707

PCT Pub. Date: Sep. 19, 2002

(65) Prior Publication Data

US 2004/0123403 A1 Jul. 1, 2004

(30) Foreign Application Priority Data

| Mar. 9, 2001 | (CH) | 0440/01 |
| May 7, 2001 | (CH) | 0822/01 |
| Jul. 25, 2001 | (CH) | 1386/01 |

(51) Int. Cl.$^7$ .................. C09B 29/42; C09B 33/12; D06P 3/00
(52) U.S. Cl. .................. 534/758; 534/772; 524/190
(58) Field of Search .................. 534/758, 772; 524/190

(56) References Cited

U.S. PATENT DOCUMENTS

| 5,038,415 A | * | 8/1991 | Ueda et al. | 8/639 |
| 5,151,506 A | * | 9/1992 | Bach et al. | 534/772 |
| 5,550,098 A | * | 8/1996 | Aso et al. | 503/227 |

FOREIGN PATENT DOCUMENTS

| EP | 0763576 | 3/1997 |
| EP | 1041121 | * 10/2000 |
| GB | 1296857 | 11/1972 |
| GB | 1361250 | 7/1974 |
| JP | 08-108637 | * 4/1996 |

* cited by examiner

Primary Examiner—Fiona T. Powers
(74) Attorney, Agent, or Firm—Kevin T. Mansfield

(57) ABSTRACT

The present invention relates to pyrifone azo dyes of formula (1), wherein A is the radical of a diazo component of the benzene, naphthalene, diphenyl, azobenzene, thiophene, benzothiazole, benzoisothiazole, thiadiazole, indazole, benzotriazole, pyrazole, anthraquinone, naphttholic acid imide, chromone, phthalimide or diphenylene oxide series, $R_1$ is hydrogen, unsubstituted or hydroxyl- or phenyl-substituted $C_1$–$C_6$alkyl, it being possible for the alkyl chain to be interrupted from $C_3$ upwards by one or more oxygen atoms, or has the meanings of $R_2$, $R_2$ is a radical of formulae (2), (3), (4), (5), (6), or (7), wherein B is a bridging member, $R_4$ is alkyl or aryl, $R_5$ and $R_6$ are each independently of the other alkyl, aryl or heteroaryl and A is as defined for formula (1), or $R_1$ and $R_2$ toghether with the nitrogen atom in $NR_1R_2$ form a heterocyclic ring, Y is cyano, —$CONH_2$ or $CH_2SO_3H$, and n is an integer from 2 to 6, to a process for their preparation and to their use in the production coloured plastics or polymeric color particles.

7 Claims, No Drawings

PYRIDONE DYES, A PROCESS FOR THEIR PREPARATION AND THEIR USE IN THE PRODUCTION OF COLORED PLASTICS OR POLYMERIC COLOR PARTICLES

The present invention relates to pyridone azo dyes, to their preparation and to their use in the production of coloured plastics or polymeric colour particles.

Pyridone azo dyes and their use in dyeing semi-synthetic or synthetic hydrophobic fibre materials are known. When the known pyridone azo dyes are used for mass-colouring synthetic materials (plastics), it has been shown, however, that those dyes do not always fully satisfy the highest demands, especially in respect of heat resistance, migratability and/or tinctorial strength. There is therefore a need for new pyridone azo dyes that yield thermostable tinctorially strong mass-colorations and exhibit good allround fastness properties.

It has now been found, surprisingly, that the pyridone azo dyes according to the invention meet the criteria given above to a considerable degree.

The present invention accordingly relates to pyridone azo dyes of formula

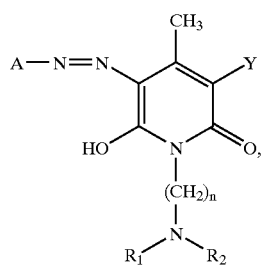
(1)

wherein

A is the radical of a diazo component of the benzene, naphthalene, diphenyl, azobenzene, thiophene, benzothiazole, benzisothiazole, thiadiazole, indazole, benzotriazole, pyrazole, anthraquinone, naphtholic acid imide, chromone, phthalimide or diphenylene oxide series, $R_1$ is hydrogen, unsubstituted or hydroxy- or phenyl-substituted $C_1$–$C_6$alkyl, it being possible for the alkyl chain to be interrupted from $C_3$ upwards by one or more oxygen atoms, or has the meanings of $R_2$, $R_2$ is a radical of formula

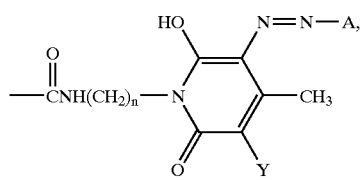
(2)

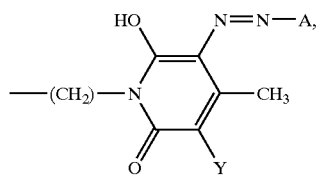
(3)

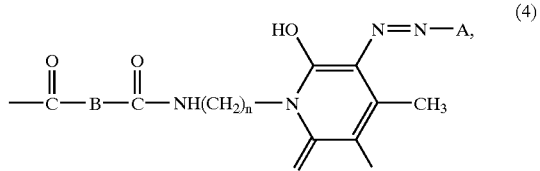
(4)

(5)

(6)

(7)

wherein B is a bridging member, $R_4$ is alkyl or aryl, $R_5$ and $R_6$ are each independently of the other alkyl, aryl or heteroaryl and A is as defined for formula (1), or $R_1$ and $R_2$ together with the nitrogen atom in —$NR_1R_2$ form a heterocyclic ring, Y is cyano, —$CONH_2$ or —$CH_2SO_3H$, and n is an integer from 2 to 6.

A is preferably the radical of a diazo component of the benzene series.

Especially preferable as A is a radical of formula

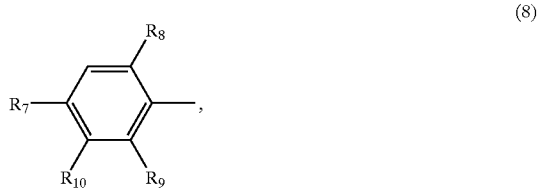
(8)

wherein $R_7$ is hydrogen or halogen, $R_8$ is hydrogen, halogen, cyano, —$CF_3$, —$COOR_{11}$ wherein $R_{11}$ is $C_1$–$C_4$alkyl and the alkyl chain can be interrupted by oxygen, or is benzyl or —$SO_2R_{12}$ wherein $R_{12}$ is —$NR_{13}R_{14}$ or phenyl and $R_{13}$ is hydrogen or $C_1$–$C_4$alkyl and $R_{14}$ is $C_1$–$C_4$alkyl or benzyl, $R_9$ is hydrogen or halogen, and $R_{10}$ is hydrogen or a radical —$SO_2$—O—$C_6H_5$.

$C_1$–$C_6$Alkyl as $R_1$ is, for example, methyl, ethyl, propyl, isopropyl, n-butyl, isobutyl, sec-butyl, tert-butyl, amyl, tert-amyl (1,1-dimethylpropyl), 1,1,3,3-tetramethylbutyl, hexyl, 1-methylpentyl, neopentyl, cyclopentyl, cyclohexyl, and the associated isomers and especially methyl. $R_1$ is preferably methyl, ethyl or the radical —CO—$R_6$ (7) and especially hydrogen.

Alkyl in the definition of $R_4$, $R_5$ and $R_6$ is, for example, $C_1$–$C_4$alkyl, such as methyl, ethyl, propyl, isopropyl, n-butyl, isobutyl, sec-butyl and tert-butyl, and also $C_1$–$C_4$alkyl substituted by $C_1$–$C_2$alkoxy or by benzyloxy, or $C_5$–$C_6$cycloalkyl, such as cyclopentyl and cyclohexyl.

Aryl in the definition of $R_4$, $R_5$ and $R_6$ is, for example, phenyl or naphthyl.

A heterocyclic ring formed by $R_1$, $R_2$ and the nitrogen atom in —$NR_1R_2$ is, for example, a heterocyclic ring of the phthalimidyl, lactam or saccharin series.

Heteroaryl in the definition of $R_5$ is, for example, thiazolyl, triazolyl or thiadiazolyl.

Heteroaryl in the definition of $R_6$ is, for example, thiophene or furan.

$C_1$–$C_4$Alkyl as $R_{11}$, $R_{13}$ and $R_{14}$ is methyl, ethyl, propyl, isopropyl, n-butyl, isobutyl, sec-butyl or tert-butyl.

Y is preferably cyano.

Halogen as $R_7$, $R_5$ and $R_5$ is bromine, iodine and especially chlorine.

The bridging member B is, for example, phenylene, naphthylene, thienyl or furyl.

n is preferably a number from 2 to 4, especially 2 or 3.

Special preference is given to pyridone azo dyes of formulae

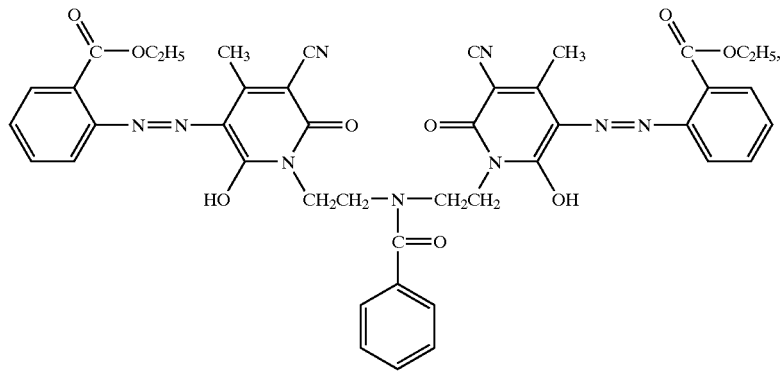

(10)

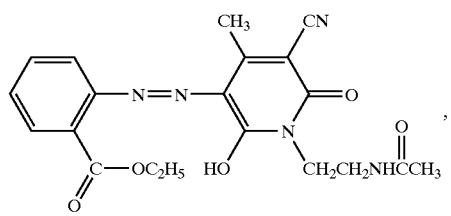

(11)

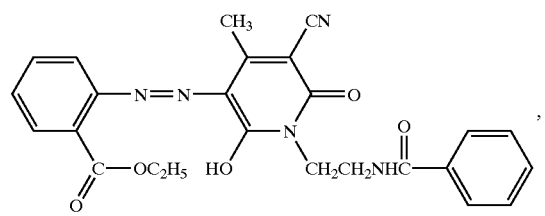

(12)

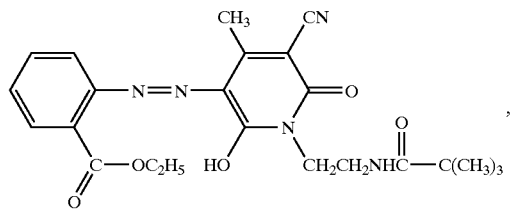

(13)

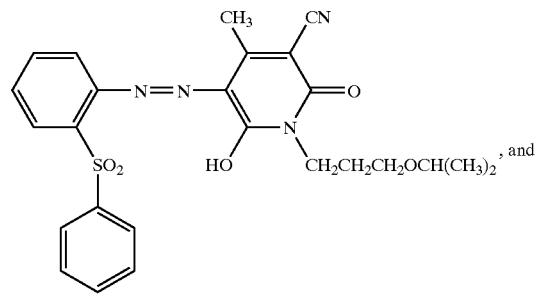

(14)

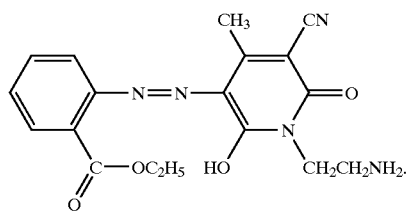

(15)

The present invention relates also to a process for the preparation of the pyridone azo dyes of formula (1) according to the invention.

The dyes are prepared, for example, as follows: a compound of formula

A-NH$_2$ (50)

is diazotised in accordance with a customary procedure and then coupled to a coupling component of formula

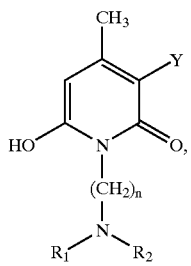

(51)

A, $R_1$, $R_2$, Y and n being as defined above for formula (1).

The diazotisation of the compound of formula (50) is carried out in a manner known per se, for example with sodium nitrite in an acidic, e.g. hydrochloric-acid-containing or sulfuric-acid-containing, aqueous medium. The diazotisation may, however, also be carried out using other diazotisation agents, e.g. using nitrosylsulfuric acid. In the diazotisation, an additional acid may be present in the reaction medium, e.g. phosphoric acid, sulfuric acid, acetic acid, propionic acid, hydrochloric acid or a mixture of such acids, e.g. a mixture of propionic acid and acetic acid. The diazotisation is advantageously carried out at temperatures of from −10 to 30° C., for example from −10° C. to room temperature.

The coupling of the diazotised compound of formula (50) to the coupling component of formula (51) is likewise effected in known manner, for example in an acidic, aqueous or aqueous-organic, medium, advantageously at temperatures of from −10 to 30° C., especially below 10° C. Examples of acids used are hydrochloric acid, acetic acid, propionic acid, sulfuric acid or phosphoric acid.

The compounds of formula (50) are known or can be prepared in a manner known per se.

The coupling components of formula (51) are known or can be prepared in a manner known per se, for example by reacting a compound of formula

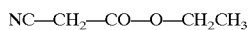

NC—CH$_2$—CO—O—CH$_2$CH$_3$ (52)

first with a compound of formula

H$_2$N—(CH$_2$)$_2$—NH$_2$ (53)

and then with a compound of formula

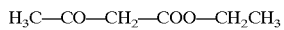

H$_3$C—CO—CH$_2$—COO—CH$_2$CH$_3$ (54)

to form a compound of formula (55)

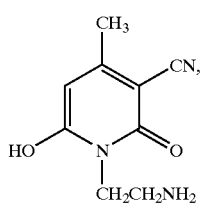

or, for example, by reacting 2 mol of a compound of formula

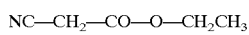

NC—CH$_2$—CO—O—CH$_2$CH$_3$ (52)

first with a compound of formula

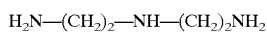

H$_2$N—(CH$_2$)$_2$—NH—(CH$_2$)$_2$NH$_2$ (56)

and then with 2 mol of a compound of formula

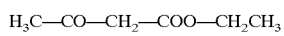

H$_3$C—CO—CH$_2$—COO—CH$_2$CH$_3$ (54)

to form a compound of formula (57)

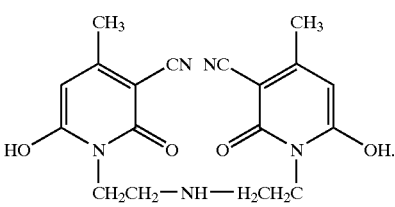

Starting from the compounds of formulae (55) and (57), the corresponding compounds of formula (51) can then be prepared in a manner known per se by the further reaction of the amino group, for example with benzoyl chloride or acetyl chloride.

The compounds of formulae (52) to (54) and (56) are known and can be prepared in a manner known per se.

The present invention relates also to a process for the production of coloured plastics or polymeric colour particles, which comprises mixing together a high molecular weight organic material and a tinctorially effective amount of at least one pyridone azo dye of formula (1).

The colouring of high molecular weight organic substances with the pyridone azo dye of formula (1) is carried out, for example, by mixing such a pyridone azo dye into those substrates using roll mills, mixing apparatus or grinding apparatus, with the result that the pyridone azo dye is dissolved or finely dispersed in the high molecular weight material. The high molecular weight organic material with the admixed pyridone azo dye is then processed using processes known per se, for example calendering, compression moulding, extrusion, coating, spinning, casting or injection moulding, whereby the coloured material acquires its final form. It is also possible for the admixing of the pyridone azo dye to be carried out immediately prior to the actual processing step, for example by continuously feeding a pulverulent pyridone azo dye and, at the same time, a granulated or pulverulent high molecular weight organic material, and optionally also additional ingredients, e.g. additives, directly into the intake zone of an extruder, where mixing takes place just before processing. In general, however, it is preferable for the pyridone azo dye to be mixed into the high molecular weight organic material beforehand, because more even coloration of the substrates can be obtained.

It is often desirable, in order to produce non-rigid mouldings or to reduce their brittleness, to incorporate so-called plasticisers into the high molecular weight compounds prior to shaping. There may be used as plasticisers, for example, esters of phosphoric acid, phthalic acid or sebacic acid. In the process according to the invention the plasticisers may be incorporated into the polymers before or after the incorporation of the colorant. It is also possible, in order to achieve different shades of colour, to add to the high molecular weight organic materials, in addition to the pyridone azo dye of formula (1), also further pyridone azo dyes or other colorants in any desired amounts, optionally together with further additives, e.g. fillers or siccatives.

In order to improve the light fastness properties, UV absorbers are advantageously mixed into the plastics or polymeric particles to be coloured with the pyridone azo dye of formula (1) according to the invention. The amount of UV absorber can vary within a wide range; advantageously there is used from 0.01 to 1.0% by weight, especially from 0.05 to 0.6% by weight, more especially from 0.1 to 0.4% by weight, of a UV absorber, based on the weight of the plastics or polymeric particles.

Suitable UV absorbers are especially 2-(2'-hydroxyphenyl)benzotriazoles, 2-hydroxybenzophenones, esters of substituted or unsubstituted benzoic acid, acrylates, oxamides, 2-(2-hydroxyphenyl)-1,3,5-triazines, monobenzoates of resorcinol or formamidines, and a polyester UV absorber of formula

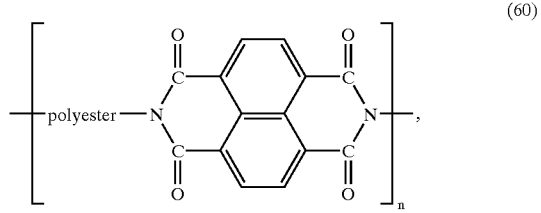

(60)

having a specific weight of from 1200 to 1400, preferably from 1300 to 1350, at 25° C.

From the class of the 2-(2'-hydroxyphenyl)benzotriazoles there may be mentioned, for example, 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphonyl)benzotriazole, 2-(3'-dodecyl-2'-hydroxy-5'-methylphenyl)benzotriazole, 2-(3'-tert-butyl-2'-hydroxy-5'-(2-iso-octyloxycarbonylethyl)phenylbenzotriazole, 2,2'-methylene-bis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300;

[R—CH$_2$CH$_2$—COO—CH$_2$CH$_2$]$_2$, wherein R=3'-tert-butyl-4'-hydroxy-5'-2H-benzotriazol-2-ylphenyl; 2-[2'-hydroxy-3'-(α,α-dimethylbenzyl)-5'-(1,1,3,3-tetramethylbutyl)phenyl]benzotriazole; and 2-[2'-hydroxy-3'-(1,1,3,3-tetramethylbutyl)-5'-(α,α-dimethylbenzyl)phenyl]benzotriazole.

From the class of the 2-hydroxybenzophenones there may be mentioned, for example, the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

From the class of the 2-(2-hydroxyphenyl)-1,3,5-triazines there may be mentioned, for example, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

From the class of the oxamides there may be mentioned, for example, 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethyloxanilide and a mixture thereof with 2-ethoxy-2'-ethyl-5,4'-di-tert-butoxanilide and mixtures of o- and p-methoxy-disubstituted oxanilides and mixtures of o- and p-ethoxy-disubstituted oxanilides.

As esters of substituted or unsubstituted benzoic acid there may be mentioned, for example, 4-tert-butylphenyl salicylate, phenyl salicylates, octylphenyl salicylates, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate or 2-methyl-4,6-di-tert-butylphenyl 3,5-di-tert-butyl-4-hydroxybenzoate.

From the class of the acrylates there may be mentioned, for example, ethyl-α-cyano-β,β-diphenylacrylate, isooctyl-α-cyano-β,β-diphenylacrylate, methyl-α-carbomethoxycinnamate, methyl-α-cyano-β-methyl-p-methoxycinnamate, butyl-α-cyano-β-methyl-p-methoxycinnamate, methyl-α-carbomethoxy-p-methoxycinnamate or N—(β-carbomethoxy-β-cyanovinyl)-2-methylindoline.

A resorcinol monobenzoate is, for example, a compound of formula

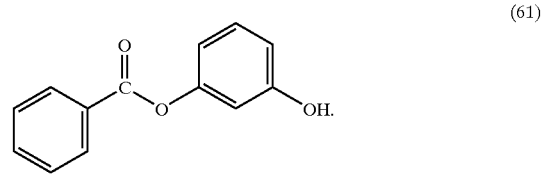

(61)

A formamidine is, for example, a compound of formula

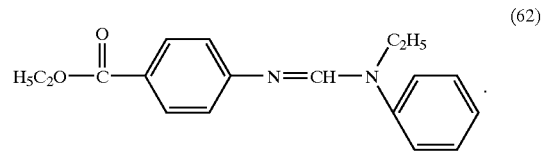

(62)

Preference is given to the colouring of thermoplastic plastics, especially in the form of fibres, granules or mouldings, for example containers for solid or liquid substances, for example bottles. Preferred high molecular weight organic materials to be coloured according to the invention are very generally polymers having a dielectric constant of ≧2.5, especially polyester, polycarbonate (PC), polystyrene (PS), polymethyl methacrylate (PMMA), polyamide, polyethylene, polypropylene, styrene/acrylonitrile (SAN) or acrylonitrile/butadiene/styrene (ABS). Polyester and polyamide are especially preferred. Very special preference is given to linear aromatic polyesters obtainable by polycondensation of terephthalic acid or naphthalene-2,6-dicarboxylic acid and glycols, especially ethylene glycol, or condensation products of terephthalic acid and 1,4-bis(hydroxymethyl)cyclohexane, for example polyethylene terephthalate (PET), polyethylene naphthalene-2,6-dicarboxylate (PEN) or polybutylene terephthalate (PBTP); also polycarbonates, e.g. those from α,α-dimethyl-4,4-dihydroxy-diphenylmethane and phosgene, or polymers based on polyvinyl chloride and on polyamides, e.g. polyamide-6 or polyamide-6,6.

The pyridone azo dyes according to the invention impart to the mentioned materials, especially to polyester material, tinctorially strong, level colour shades having very good in-use fastness properties, especially good light fastness and high-temperature light fastness. Special mention may be made of the good migration fastness and thermomigration fastness of the dyeings obtained.

The invention relates also to a process for the production of coloured plastics or polymeric colour particles, which comprises using a combination of a pyridone azo dye of formula (1) and a UV absorber, wherein the meanings and preferred meanings given above for the pyridone azo dyes of formula (1) and the UV absorbers apply.

The invention relates also to the plastics that have been mass-coloured by the processes mentioned above.

The following Examples serve to illustrate the invention. Unless otherwise indicated, the parts are parts by weight and the percentages are percentages by weight. The temperatures are given in degrees Celsius. The relationship between parts by weight and parts by volume is the same as that between grams and cubic centimeters.

EXAMPLE 1

(A) 140.0 ml of water are placed in the reactor vessel and cooled to 0–5° C. In the course of 30 minutes, 405.2 ml of ethylenediamine and then 215.4 ml of ethyl cyanoacetate are then added dropwise, the temperature being kept below 20° C. by cooling. The reaction mixture is then stirred at 20° C. for 16 hours, the excess ethylenediamine is distilled off in vacuo at 60° C. and the mixture is stirred at 40° C. for 1 hour.

253.0 ml of ethyl acetoacetate are then added dropwise, the temperature being raised to 70° C. towards the end of the dropwise addition. As soon as the addition of the ethyl aceto-acetate is complete, 168.0 ml of a 30% aqueous ammonia solution and then 1400.0 ml of propanol are added, and the reaction mixture is stirred for 16 hours at 70–75° C. The resulting suspension is filtered, introduced into 1500.0 ml of ethanol, stirred for 14 hours at 20° C. and filtered again. The filter cake is washed with a total of 1000.0 ml of ethanol in portions and dried.

263.6 g of a compound of formula

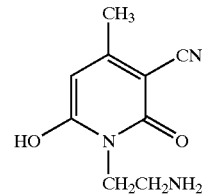

(55)

are obtained.

(B) 50.0 g of the compound of formula (55) are suspended in 500.0 ml of water, heated to 60° C., adjusted to pH 1.0 with 32% HCl and stirred for three hours at 60° C. A crystalline precipitate is then removed from the reaction mass by filtration, the mother liquor is adjusted to pH 9.0 with 30% aqueous NaOH, and 40.0 ml of benzoyl chloride are added. The reaction mixture is then stirred for 18 hours, the pH value being kept at 9.0, if necessary by the addition of HCl. 100.0 g of NaCl are then added, and the fully reacted reaction mass is adjusted to pH 0.5 with 32% HCl and stirred at 0° C. until the product has precipitated. The precipitated reaction product is filtered off with suction and dried.

93.5 g of a product containing 62.3 g of a compound of formula

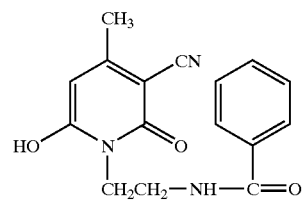

(58)

are obtained.

(C) 10.6 ml of ethyl anthranilate are placed in 110.0 ml of 98% acetic acid at from 15 to 20° C., and 22.0 g of 32% HCl are added. 17.8 ml of 4N NaNO$_2$ are then added dropwise to the reaction mass, and stirring is carried out for 1 hour at 10–15° C. The excess nitrite is then destroyed with sulfamic acid.

(D) 14.9 g of the compound of formula (58) prepared according to (B) are placed in 150.0 ml of water; 22.0 g of 30% aqueous NaOH are added and the mixture is heated to 50° C. 120 g of the diazo solution prepared according to (B) are then added dropwise to the resulting suspension, the temperature being kept at 15° C. by the addition of about 200.0 g of ice. Once the addition is complete, the pH value is adjusted to 5.0 and the reaction mass is stirred for 16 hours.

300.0 ml of water are then added, and the fully reacted reaction mass is heated to 70° C., filtered with suction, washed with water and dried.

20.0 g of a pyridone azo dye of formula

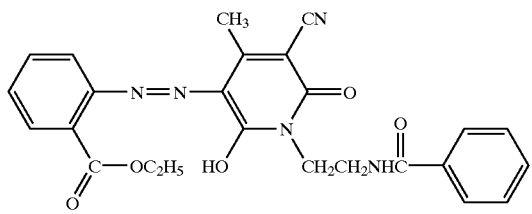

(12)

are obtained, which dyes polyester in yellow shades.

EXAMPLE 2

(A) 111.95 ml of diethylenetriamine are placed in a reaction flask and 236.95 ml of ethyl cyanoacetate are added at 20° C., the temperature rising to about 75° C. The reaction mixture is stirred for 30 minutes, and then 1000.0 ml of 94% ethanol are added and the mixture is stirred for 2 hours at 72° C. (reflux). 278.3 ml of ethyl acetoacetate, 168.0 ml of a 30% aqueous ammonia solution and 3000.0 ml of 94% ethanol are then added in succession and the mixture is stirred for a further 41 hours at reflux.

The resulting suspension is filtered with suction at 75° C., then washed with a total of 500.0 ml of 94% ethanol in portions, and then 2000.0 ml of 94% ethanol are added and the mixture is stirred for 14 hours at 20° C. The suspension is then filtered with suction, the filter cake is washed with a total of 1000.0 ml of 94% ethanol in portions and dried in vacuo.

235.6 g of a compound of formula

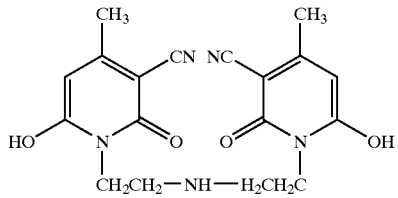

(57)

are obtained.

(B) 92.35 g of the compound of formula (57) are suspended in 1000.0 ml of water, and the suspension is heated to 60° C., adjusted to pH 1.0 with 32% HCl and stirred for three hours at 60° C. A crystalline precipitate is then removed from the reaction mass by filtration, the mother liquor is adjusted to pH 9.0 with 30% aqueous NaOH, and 40.0 ml of benzoyl chloride are added. The reaction mixture is then stirred for 18 hours, the pH value being maintained at 9.0, if necessary by the addition of HCl.

200.0 g of NaCl are then added and the fully reacted reaction mass is adjusted to pH 0.5 with 32% HCl and stirred at 0° C. until the product has precipitated. The precipitated reaction product is filtered off with suction and dried.

90.0 g of a compound of formula

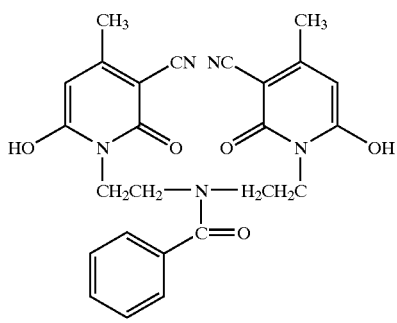

(59)

are obtained.

(C) 1.65 g of ethyl anthranilate are placed in 10.0 ml of glacial acetic acid at from 15 to 30° C., 0.6 ml of 96% sulfuric acid is added and the mixture is stirred for 30 minutes. 1.85 ml of 40% nitrosylsulfuric acid are then added dropwise over the course of 10 minutes to the reaction mass, and the mixture is stirred at 17–20° C. for 1 hour.

(D) 100.0 ml of dimethylformamide (DMF) are taken as starting material and, with stirring, 2.4 g of the compound of formula (59) and 10.0 ml of ice water are added. Then, in the course of 30 minutes, at a temperature of 5–10° C. there are added dropwise the diazo solution prepared under (C) and, at the same time, in order to maintain the pH value at 3–4, 22.0 ml of a 10% aqueous NaOH solution.

The reaction mixture is stirred for 4 hours at 0–5° C., then adjusted to pH 4.6 and stirred for a further 17 hours at 20° C. The resulting suspension is filtered with suction, washed in succession with 25.0 ml of 80% DMF, ethanol and water until pH>6 and dried.

3.3 g of a pyridone azo dye of formula

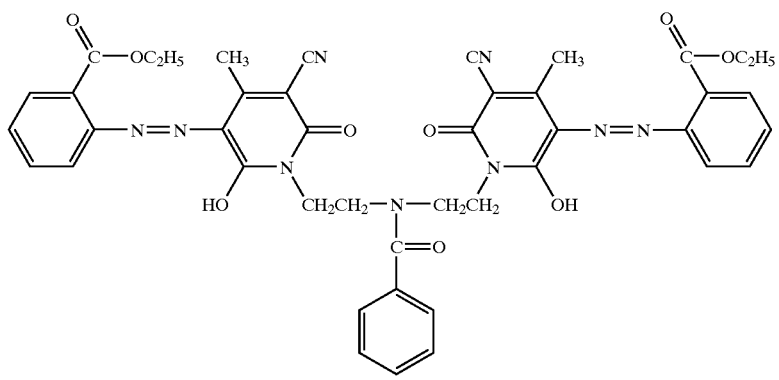

(10)

are obtained,
which dyes polyester in yellow shades.
EXAMPLES 3–185
Analogously to the processes described in Examples 1 and 2, it is also possible to prepare the following dyes listed in Tables 1 to 16, which likewise dye polyester in yellow shades:
TABLE 1
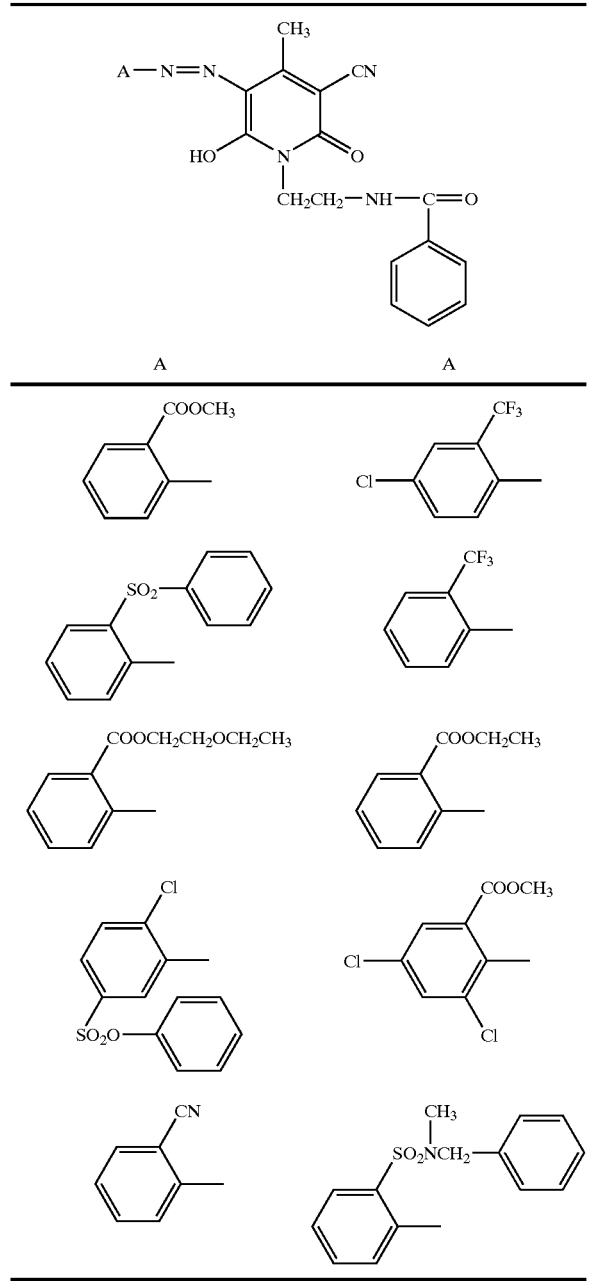
TABLE 2
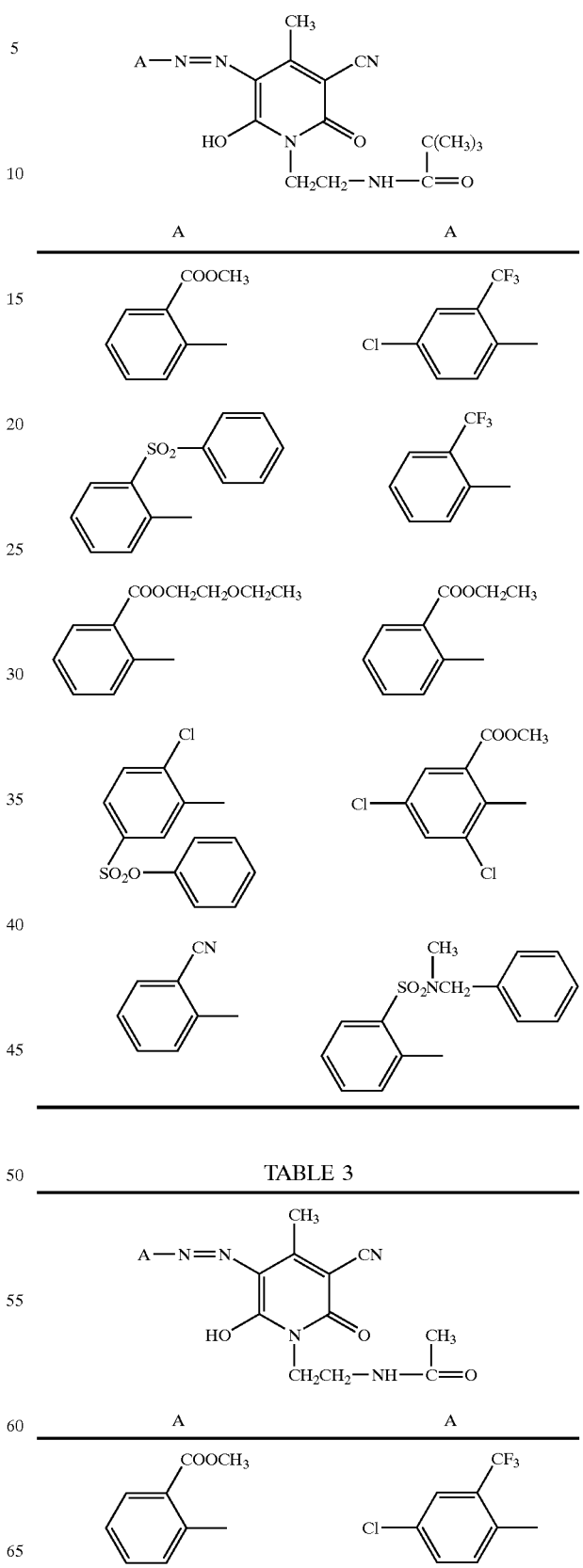
TABLE 3

TABLE 3-continued
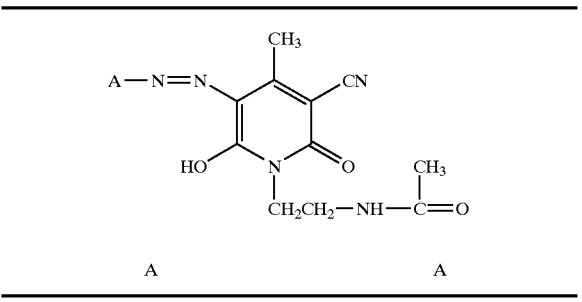
| A | A |
|---|---|
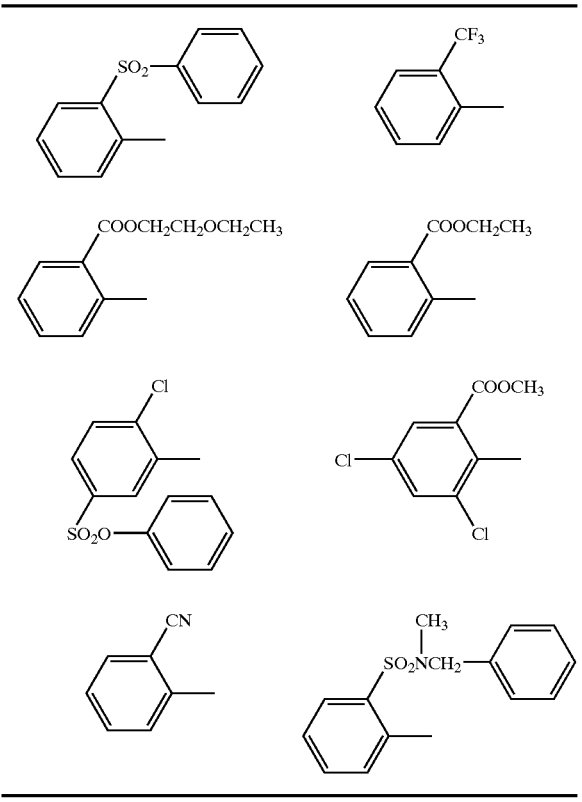
TABLE 4
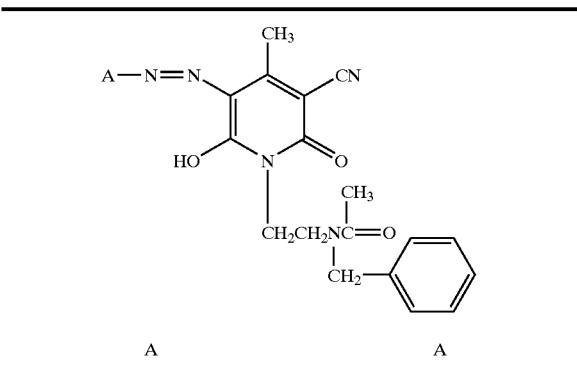
| A | A |
|---|---|
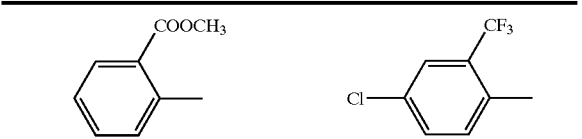
TABLE 4-continued
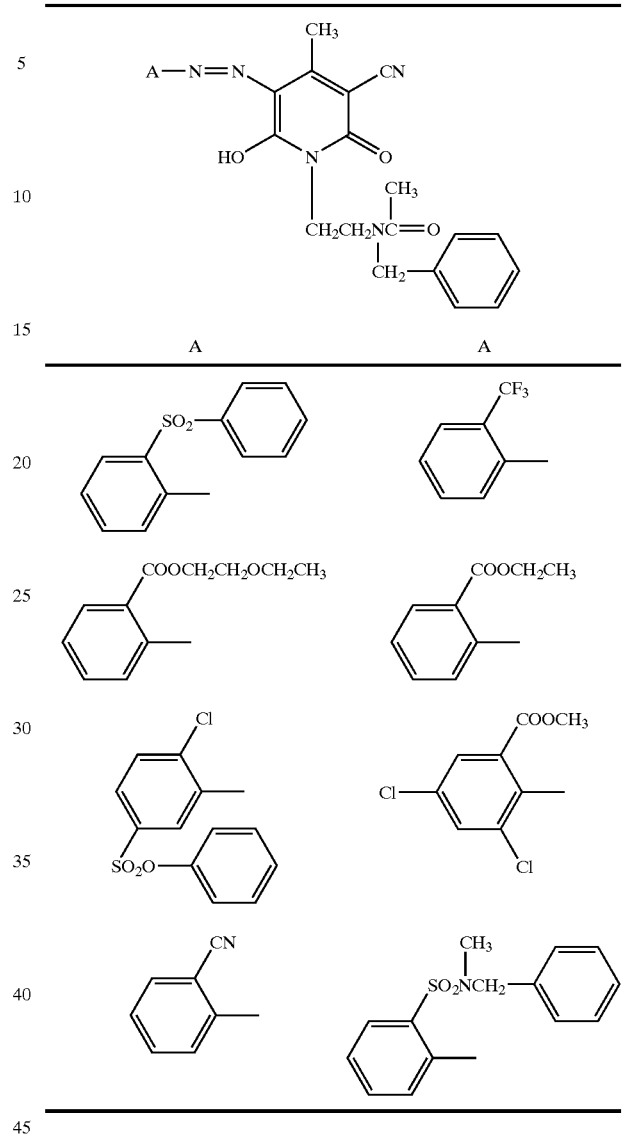
TABLE 5
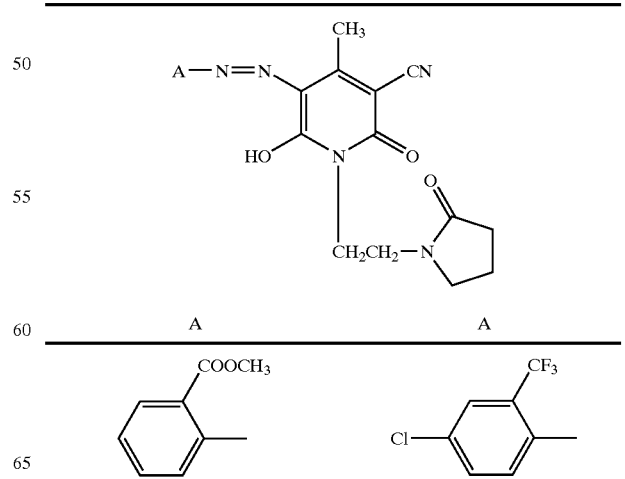

TABLE 5-continued
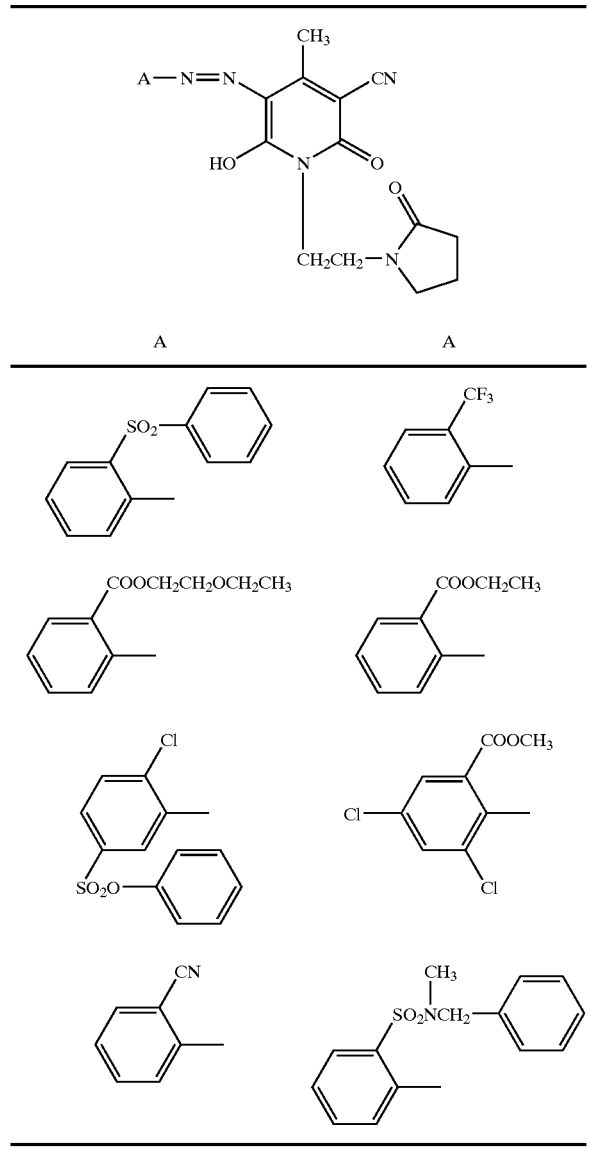
TABLE 6
TABLE 6-continued
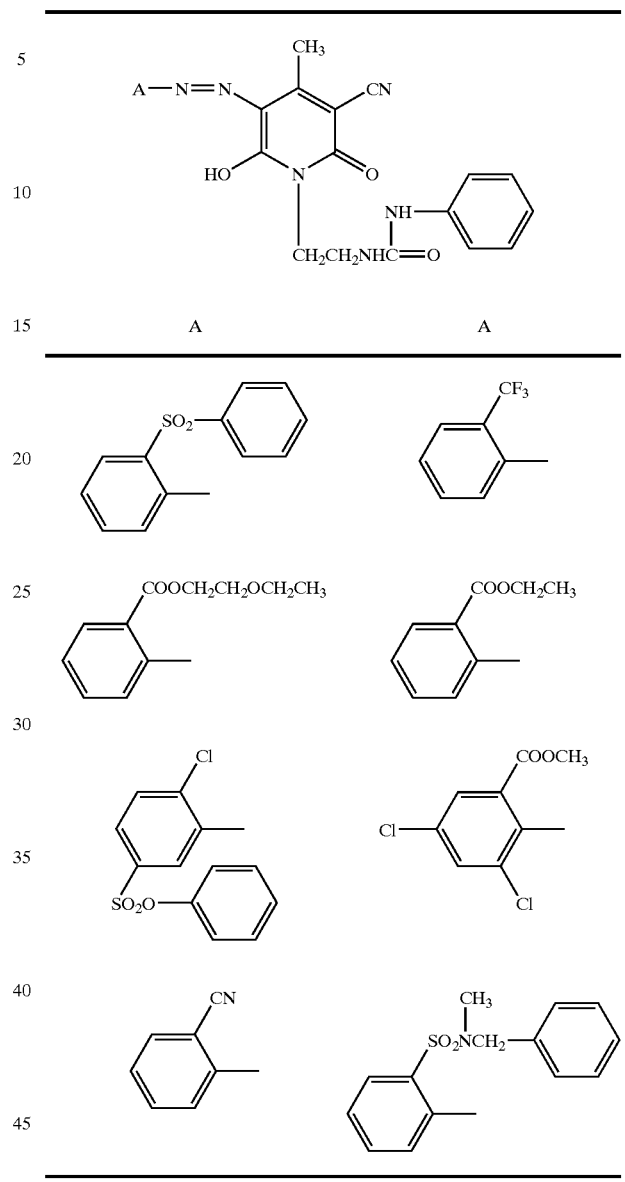
TABLE 7
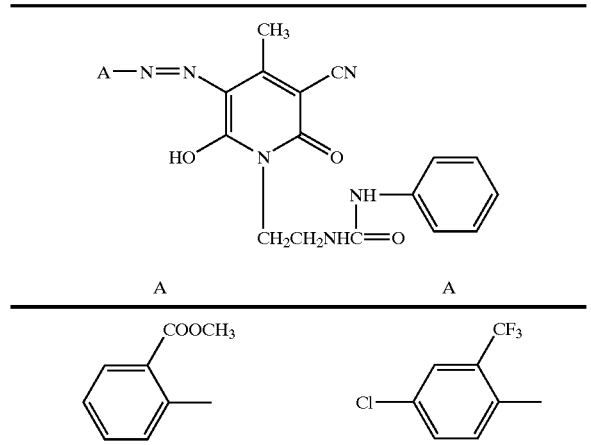
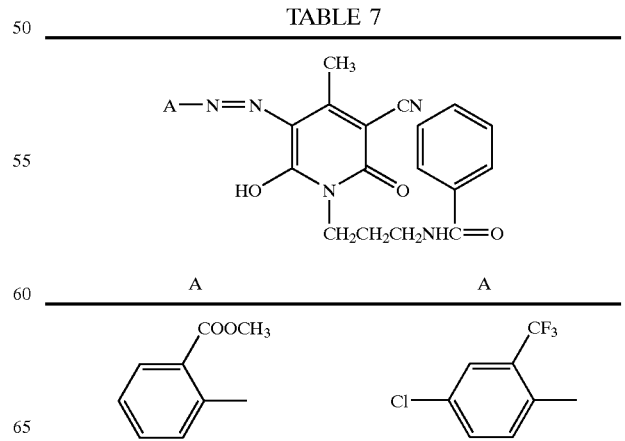

TABLE 7-continued
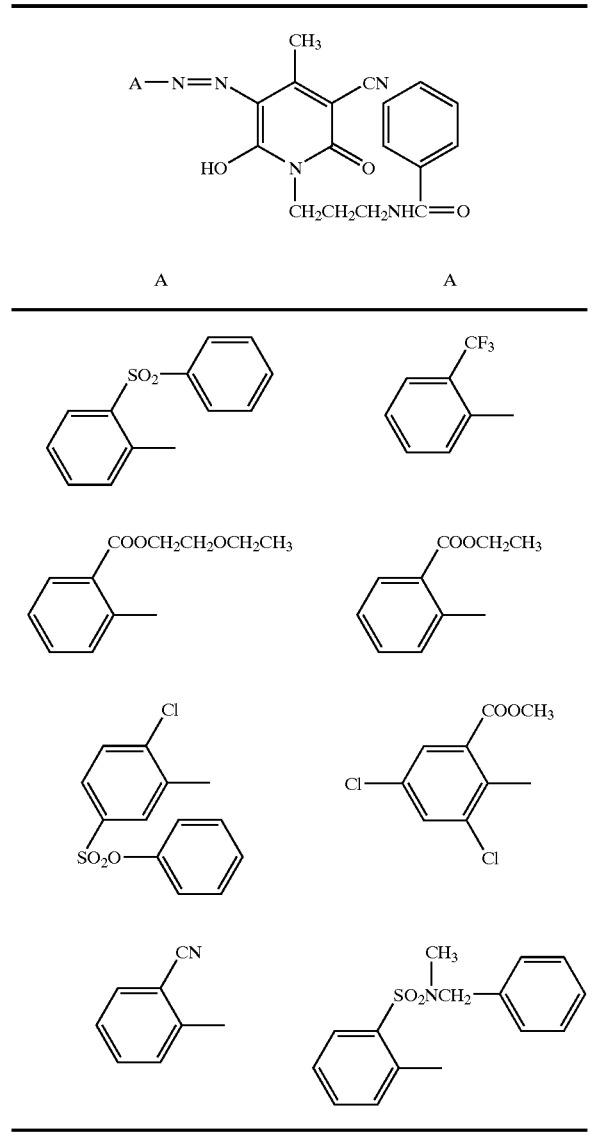
TABLE 8
TABLE 8-continued
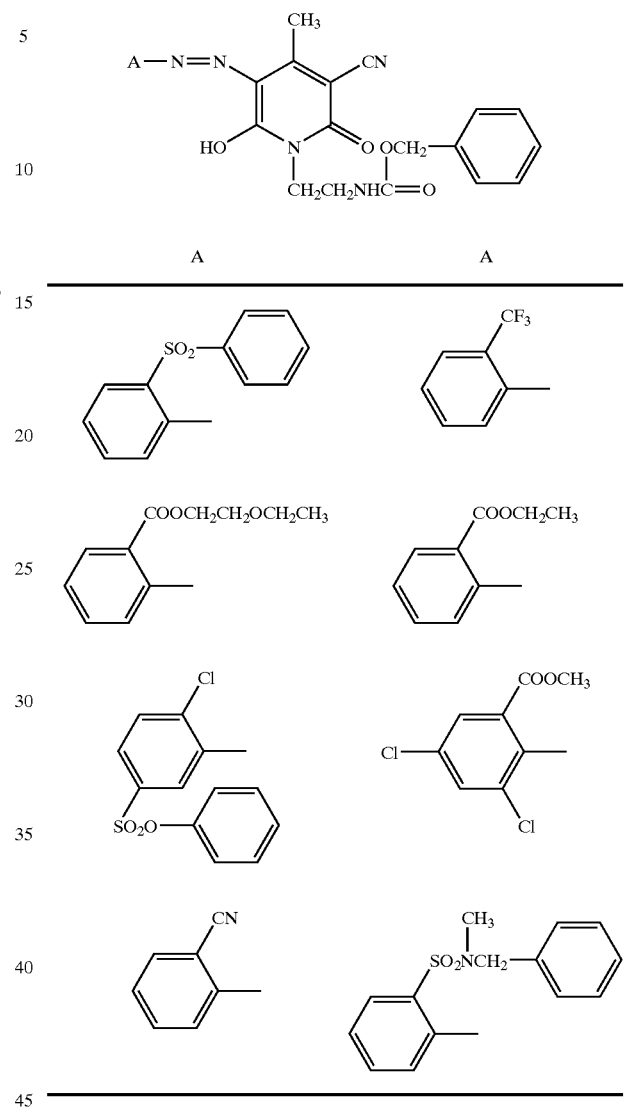
TABLE 9
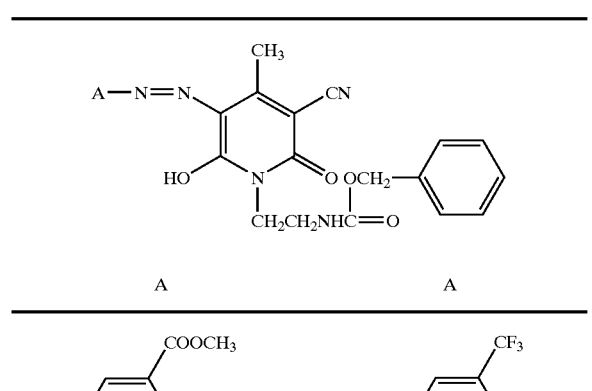
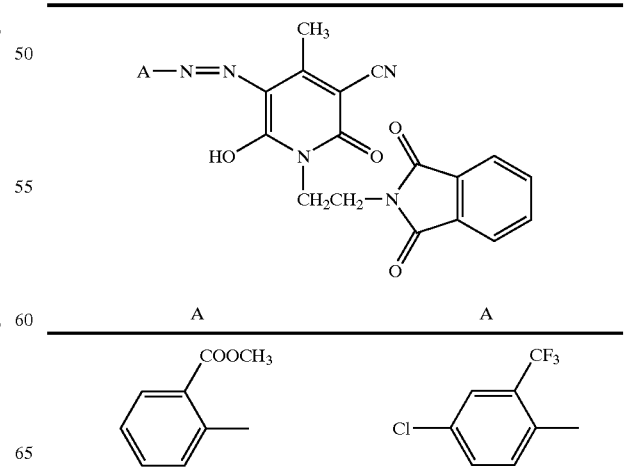

TABLE 9-continued
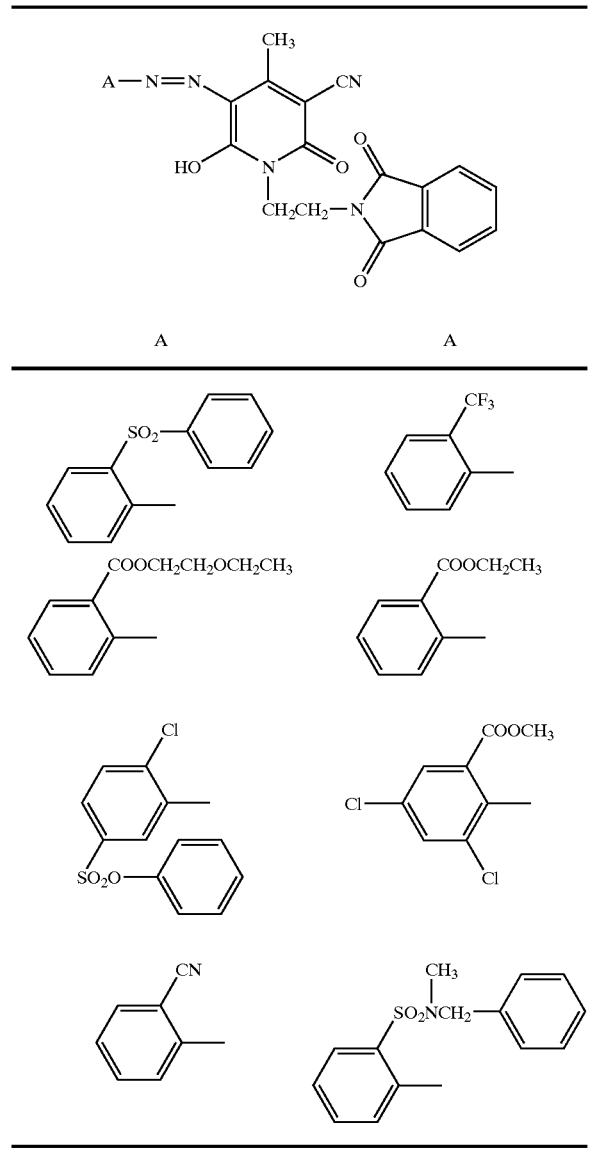
TABLE 10
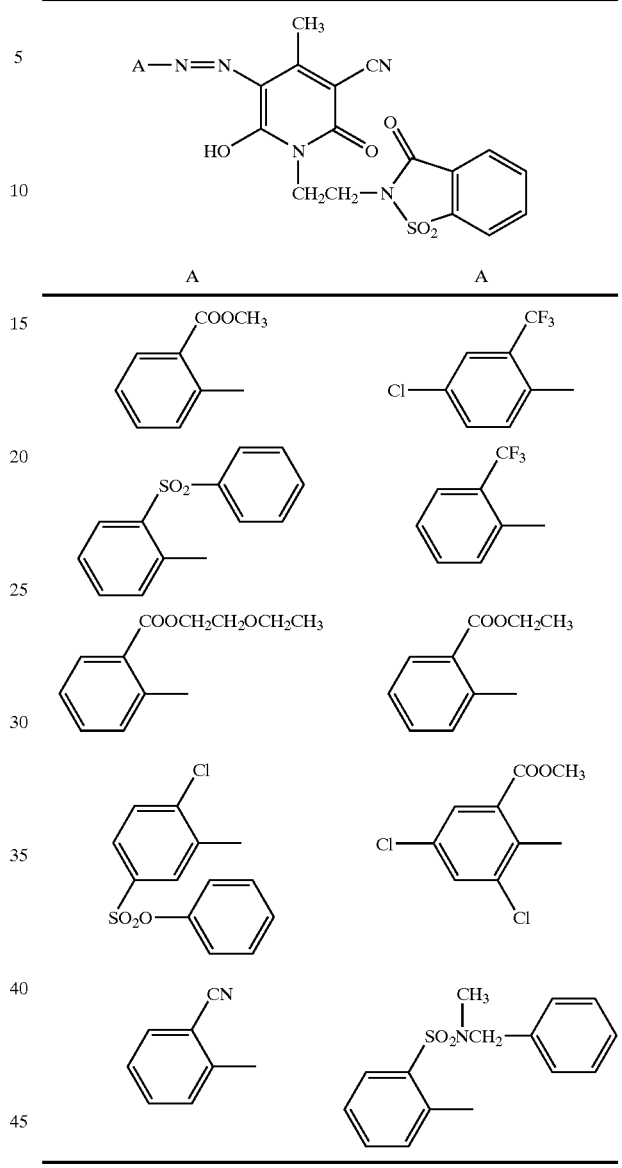
TABLE 11
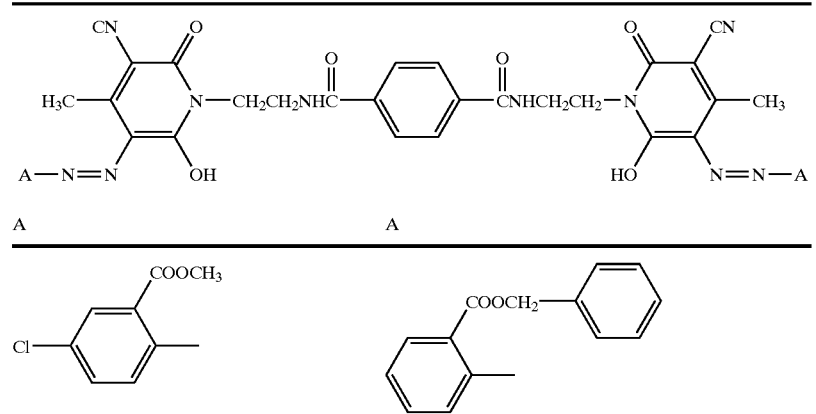

TABLE 11-continued
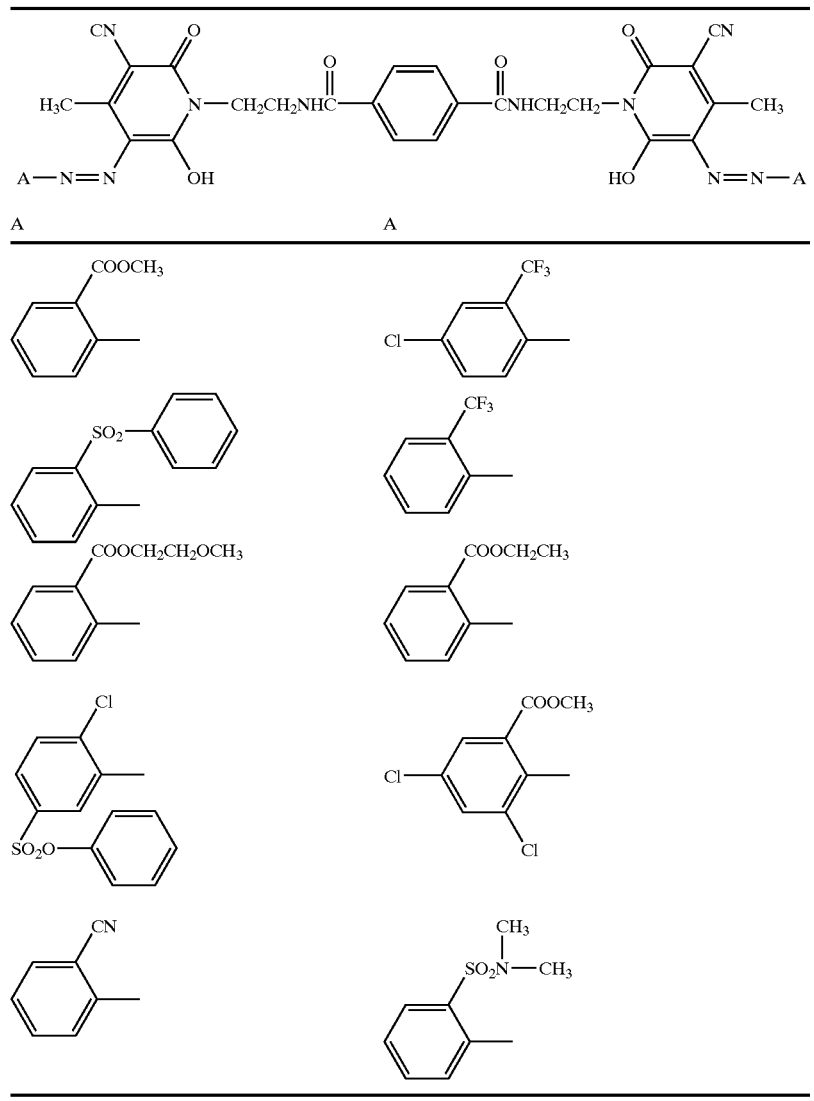
TABLE 12
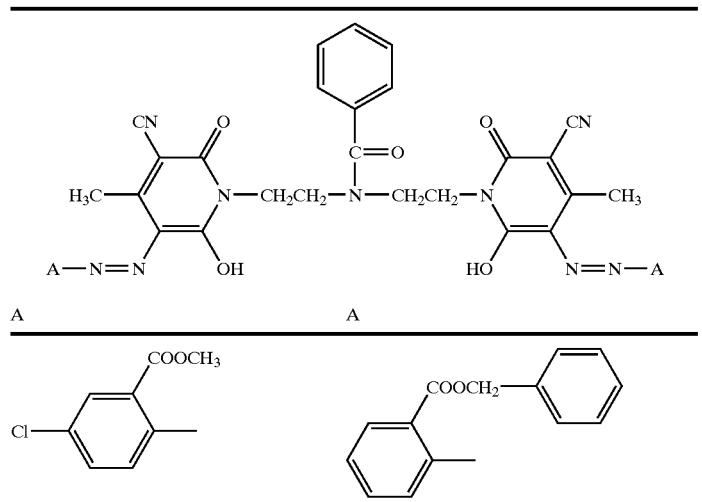

TABLE 12-continued
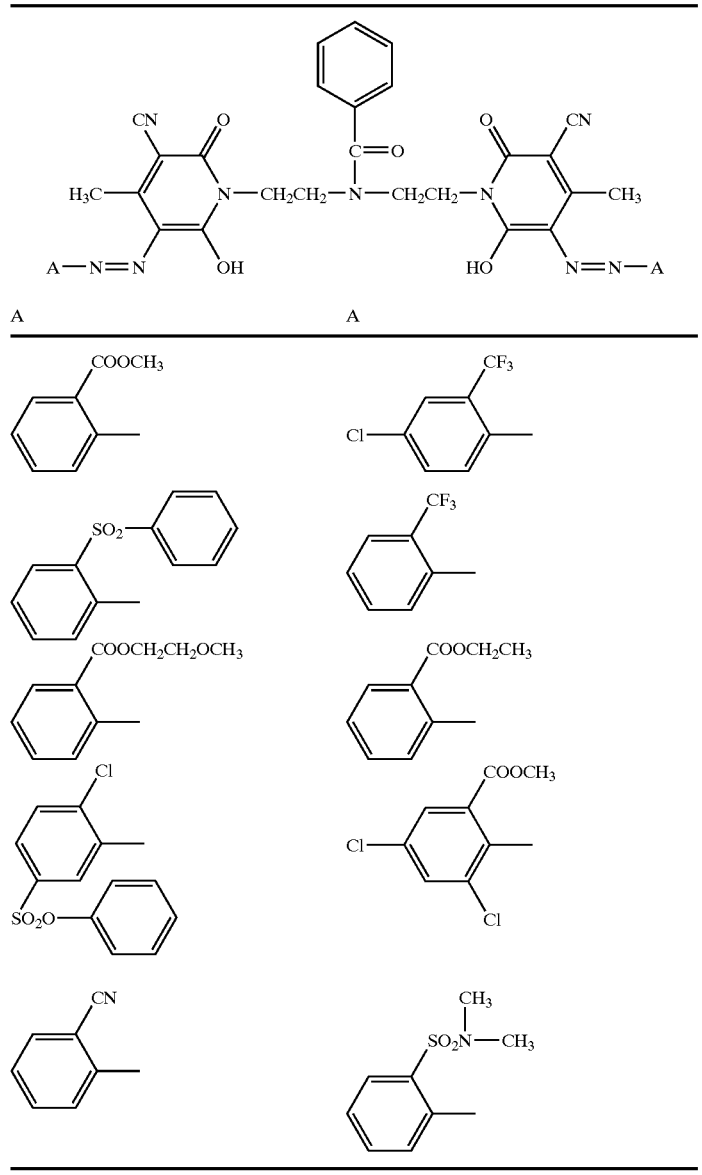
TABLE 13
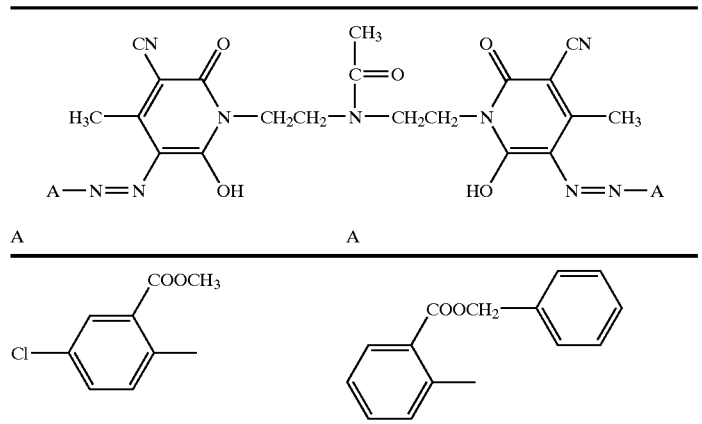

TABLE 13-continued
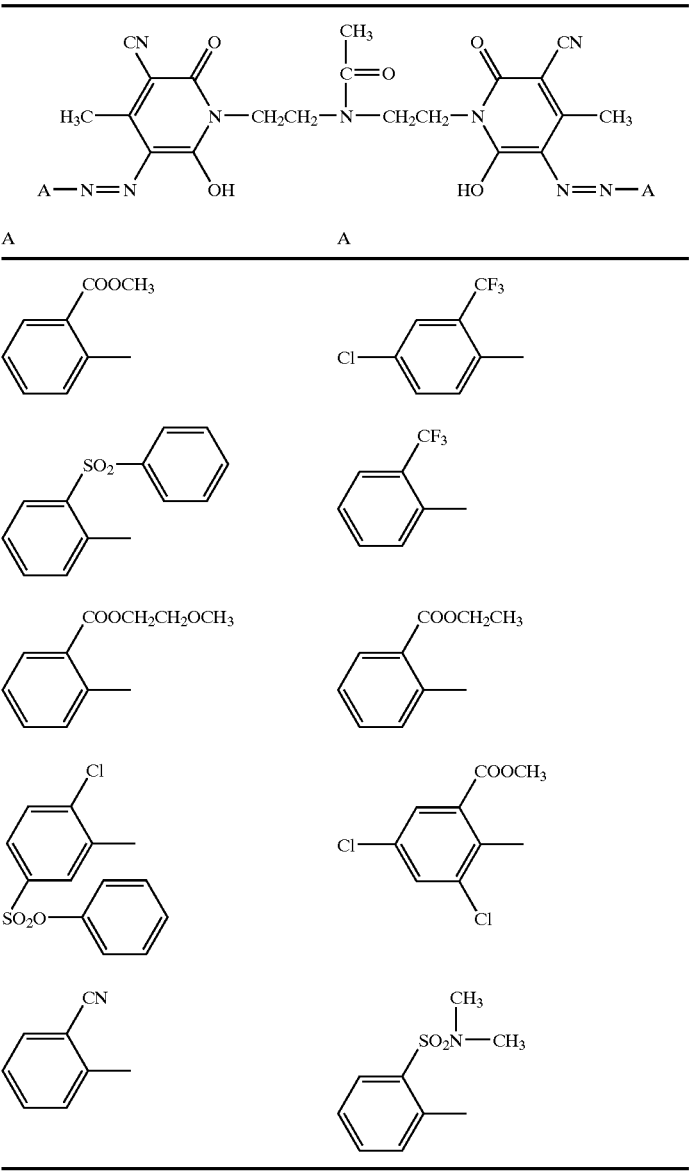
TABLE 14
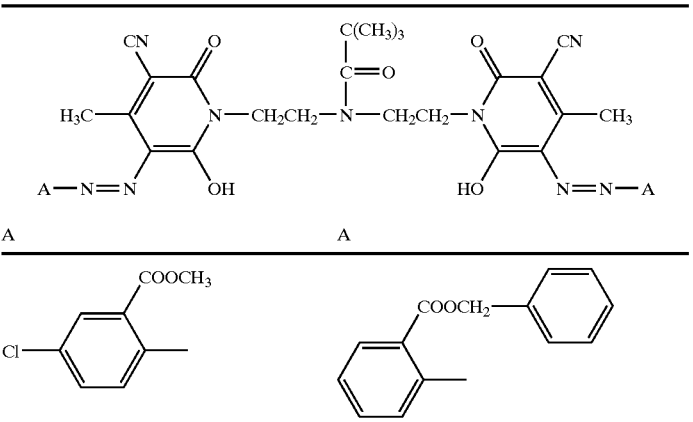

TABLE 14-continued
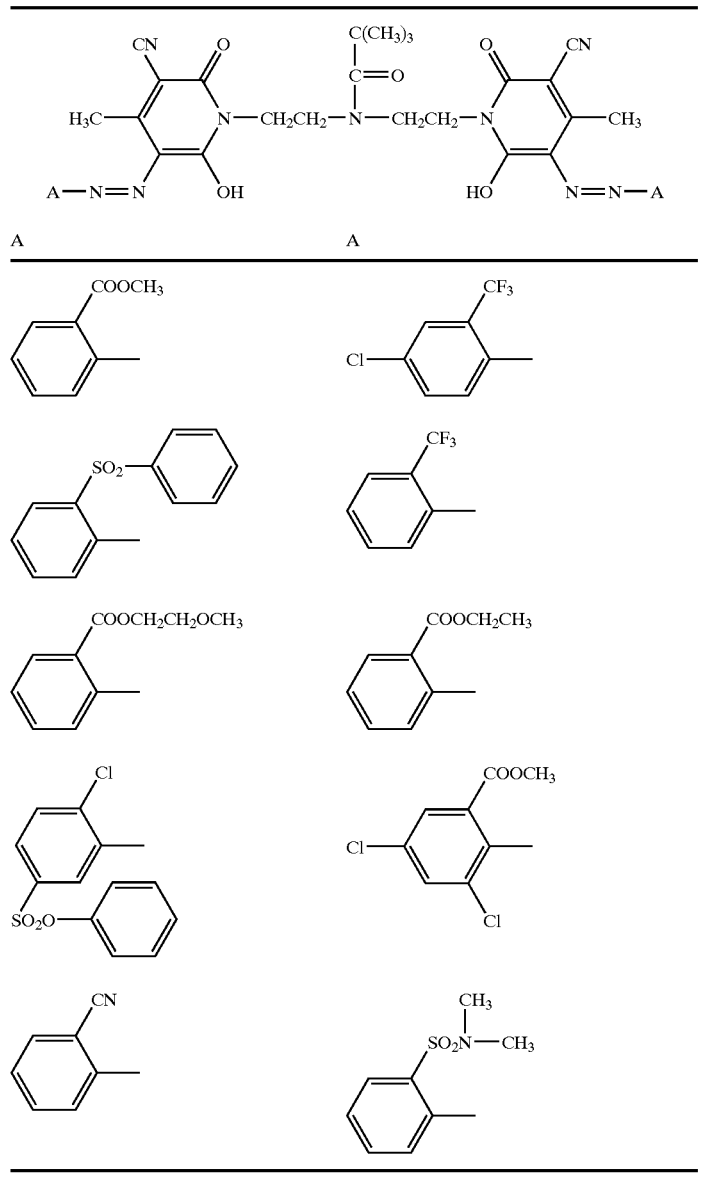
TABLE 15
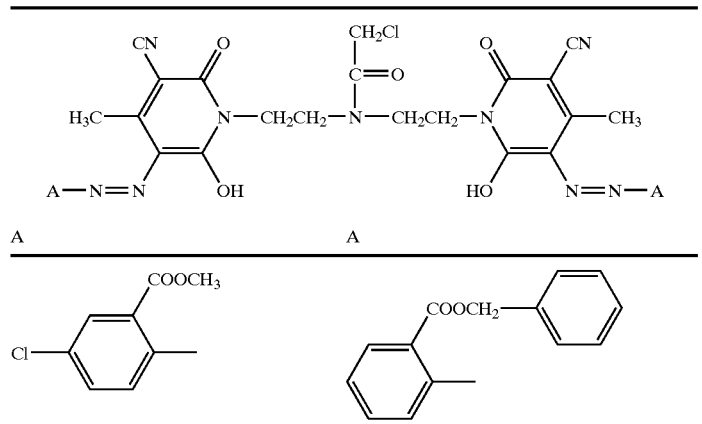

TABLE 15-continued
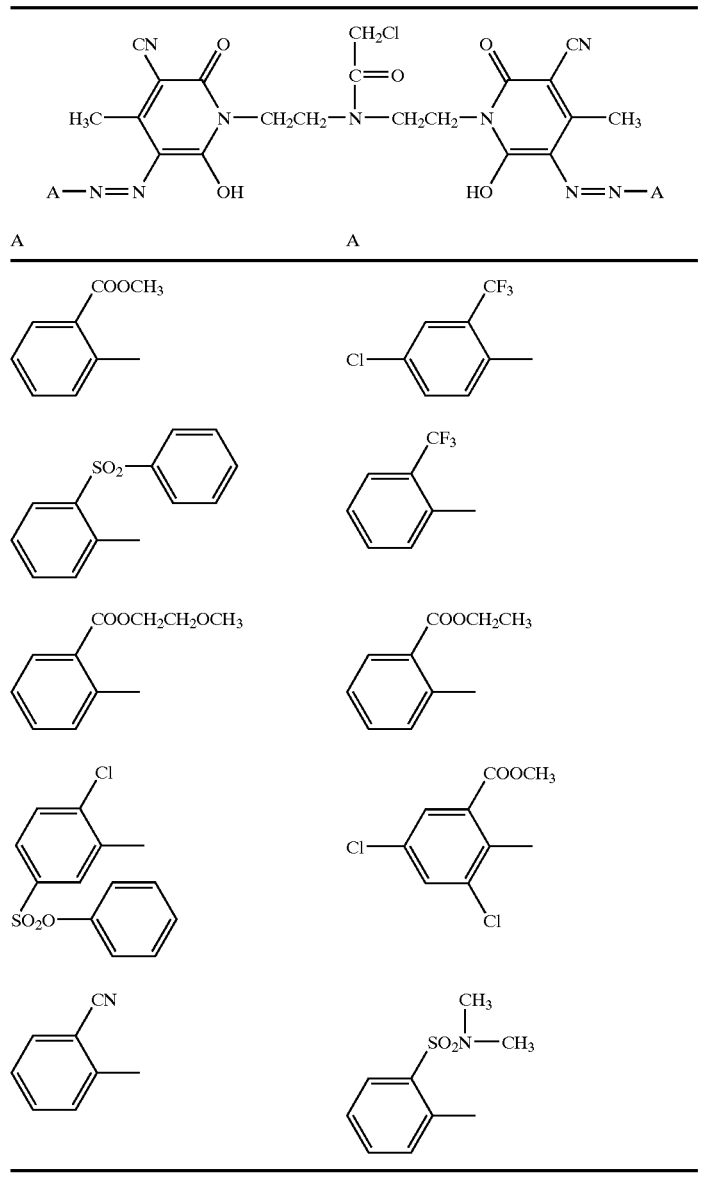
TABLE 16
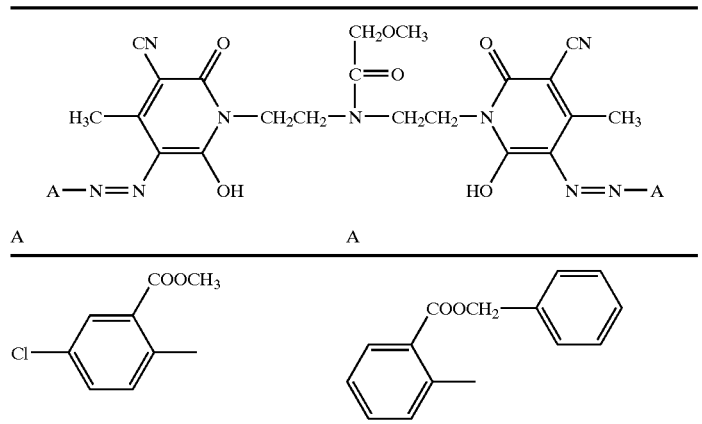

TABLE 16-continued

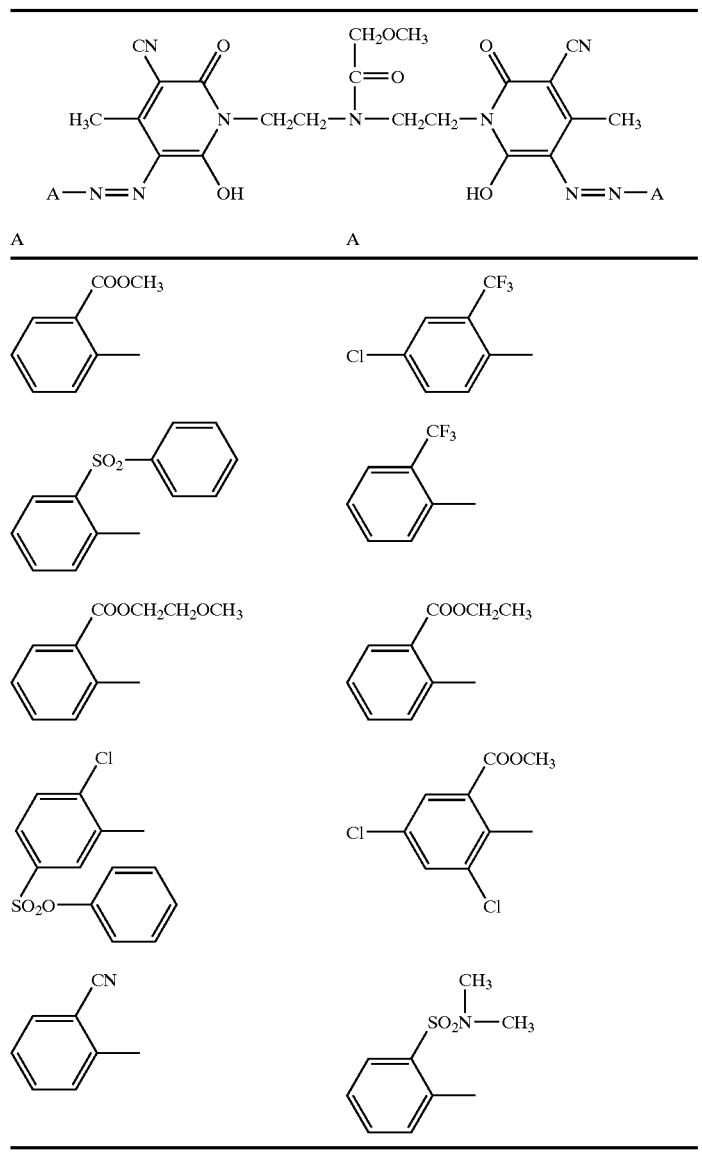

DYEING EXAMPLE 1

1200.00 g of polyester granules (PET Arnite D04-300, DSM) are pre-dried for 4 hours at 130° C. and then mixed homogeneously with 0.24 g of the pyridone azo dye of formula (14)

in a "roller rack" mixing apparatus for 15 minutes at 60 revolutions per minute.

The homogeneous mixture is extruded in an extruder (twin screw 25 mm, from Collin, D-85560 Ebersberg) with 6 heating zones at a maximum temperature of 275° C., cooled with water, granulated in a granulator (Turb Etuve TE 25, from MAPAG AG, CH-3001 Bern) and then dried at 130° C. for 4 hours.

The resulting yellow-coloured polyester granules have good allround fastness properties, especially very good light fastness and high-temperature light fastness properties.

DYEING EXAMPLE 2

1200.00 g of polyester granules (PET Arnite D04-300, DSM) are pre-dried for 4 hours at 130° C. and then mixed homogeneously with 0.60 g of the pyridone azo dye of formula (14)

and 3.60 g of a UV absorber of formula (63)

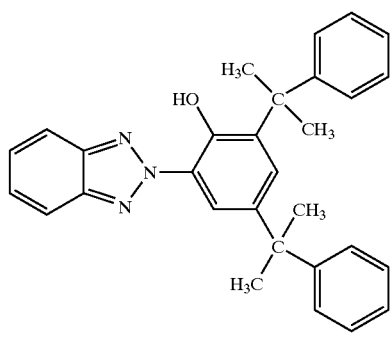

in a "roller rack" mixing apparatus for 15 minutes at 60 revolutions per minute.

The homogeneous mixture is extruded in an extruder (twin screw 25 mm, from Collin, D-85560 Ebersberg) with 6 heating zones at a maximum temperature of 275° C., cooled with water, granulated in a granulator (Turb Etuve TE 25 from MAPAG AG, CH-3001 Bern) and then dried at 130° C. for 4 hours.

The resulting yellow-coloured polyester granules have good allround fastness properties, especially very good light fastness and high-temperature light fastness properties.

What is claimed is:

1. A pyridone azo dye of formula

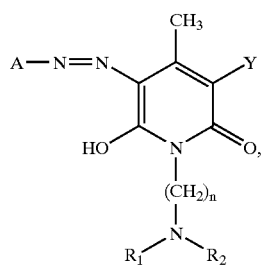

(1)

wherein

A is a radical of formula

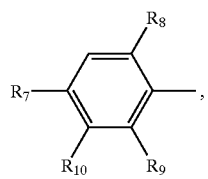

(8)

wherein

R$_7$ is hydrogen or halogen, R$_8$ is hydrogen, halogen, cyano, —CF$_3$, —COOR$_{11}$ wherein R$_{11}$ is C$_1$–C$_4$alkyl and the alkyl chain can be interrupted by oxygen, or is benzyl or —SO$_2$R$_{12}$ wherein R$_{12}$ is —NR$_{13}$R$_{14}$ or phenyl and R$_{13}$ is hydrogen or C$_1$–C$_4$alkyl and R$_{14}$ is C$_1$–C$_4$alkyl or benzyl, R$_9$ is hydrogen or halogen, and R$_{10}$ is hydrogen or a radical —SO$_2$—O—C$_6$H$_5$ R$_1$ is hydrogen, unsubstituted or hydroxy- or phenyl-substituted C$_1$–C$_6$alkyl, it being possible for the alkyl chain to be interrupted from C$_3$ upwards by one or more oxygen atoms, or has the meanings of R$_2$, R$_2$ is a radical of formula

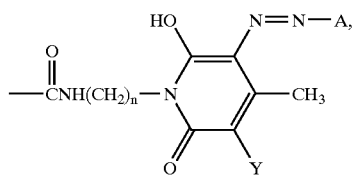

(2)

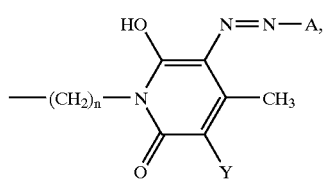

(3)

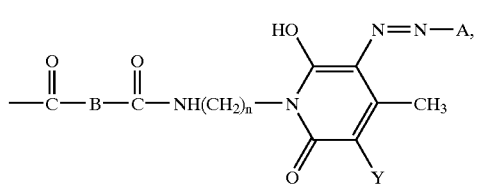

(4)

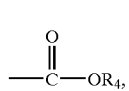

(5)

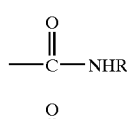

or (6)

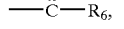

(7)

wherein

B is a bridging member, R$_4$ is alkyl or aryl, R$_5$ and R$_6$ are each independently of the other alkyl, aryl or heteroaryl and A is as defined for formula (1), or R$_1$ and R$_2$ together with the nitrogen atom in —NR$_1$R$_2$ form a heterocyclic ring, Y is cyano, —CONH$_2$ or —CH$_2$SO$_3$H, and n is an integer from 2 to 6.

2. A pyridone azo dye according to claim 1 of formula

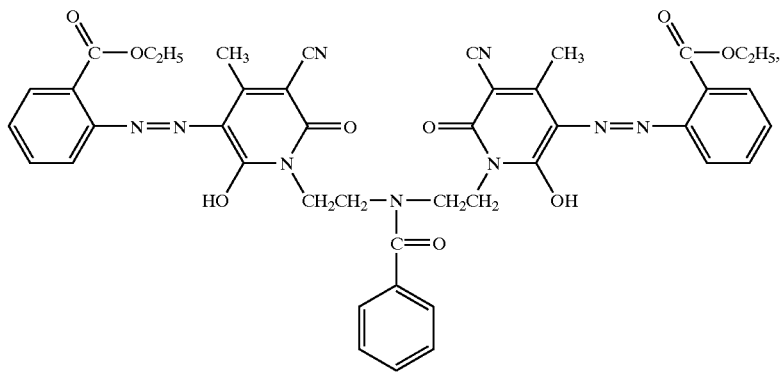

(10)

-continued (11)

(12)

(13)

3. A process for the preparation of a pyridone azo dye of formula (1) according to claim 1, in which process a compound of formula

A-NH$_2$     (50)

wherein

A is a radical of formula wherein
R$_7$ is hydrogen or halogen, R$_8$ is hydrogen, halogen, cyano, —CF$_3$, —COOR$_{11}$ wherein R$_{11}$ is C$_1$–C$_4$alkyl and the alkyl chain can be interrupted by oxygen, or is benzyl or —SO$_2$R$_{12}$ wherein R$_{12}$ is —NR$_{13}$R$_{14}$ or phenyl and R$_{13}$ is hydrogen or C$_1$–C$_4$alkyl and R$_{14}$ is C$_1$–C$_4$alkyl or benzyl, R$_9$ is hydrogen or halogen, and R$_{10}$ is hydrogen or a radical —SO$_2$—O—C$_6$H$_5$ is diazotised in accordance with a customary procedure and then coupled to a coupling component of formula (51)

wherein
R$_1$ is hydrogen, unsubstituted or hydroxy- or phenyl-substituted C$_1$–C$_6$alkyl, it being possible for the alkyl chain to be interrupted from C$_3$ upwards by one or more oxygen atoms, or has the meanings of R$_2$, R$_2$ is a radical of formula (2)

(3)

(4)

(5)

(6)

(7)

wherein
B is a bridging member, R$_4$ is alkyl or aryl, R$_5$ and R$_6$ are each independently of the other alkyl, aryl or heteroaryl and A is as defined for formula (1), or
R$_1$ and R$_2$ together with the nitrogen atom in —NR$_1$R$_2$ form a heterocyclic ring,
Y is cyano, —CONH$_2$ or —CH$_2$SO$_3$H, and n is an integer from 2 to 6.

4. A process for the production of coloured plastics or polymeric colour particles, which comprises incorporating one or more pyridone azo dyes of formula (1) according to claim 1 into those materials.

5. A process for the production of coloured plastics or polymeric colour particles, which comprises using a combination of a pyridone azo dye of formula (1) according to claim 1 and a UV absorber.

6. Plastics or polymeric colour particles coloured according to claim 4.

7. Plastics or polymeric colour particles coloured according to claim 5.

* * * * *